United States Patent
Marvin et al.

(10) Patent No.: US 9,020,826 B2
(45) Date of Patent: Apr. 28, 2015

(54) DIRECT CONNECTIVITY SYSTEM FOR HEALTHCARE ADMINISTRATIVE TRANSACTIONS

(75) Inventors: William F. Marvin, Philadelphia, PA (US); Christopher D. Seib, Costa Mesa, CA (US)

(73) Assignee: Accenture Global Services Limited, Dublin (IE)

( * ) Notice: Subject to any disclaimer, the term of this patent is extended or adjusted under 35 U.S.C. 154(b) by 1884 days.

(21) Appl. No.: 11/167,548

(22) Filed: Jun. 27, 2005

(65) Prior Publication Data

US 2005/0288972 A1 Dec. 29, 2005

Related U.S. Application Data

(60) Provisional application No. 60/583,453, filed on Jun. 28, 2004.

(51) Int. Cl.
| | |
|---|---|
| *G06Q 40/08* | (2012.01) |
| *G06F 19/00* | (2011.01) |
| *G06Q 10/10* | (2012.01) |
| *G06Q 30/02* | (2012.01) |
| *G06Q 50/22* | (2012.01) |

(52) U.S. Cl.
CPC .............. *G06Q 40/08* (2013.01); *G06F 19/328* (2013.01); *G06Q 10/10* (2013.01); *G06Q 30/02* (2013.01); *G06Q 50/22* (2013.01)

(58) Field of Classification Search
None
See application file for complete search history.

(56) References Cited

U.S. PATENT DOCUMENTS

| | | | |
|---|---|---|---|
| 5,301,105 A | | 4/1994 | Cummings, Jr. |
| 5,359,509 A | * | 10/1994 | Little et al. ........................ 705/2 |
| 5,544,044 A | | 8/1996 | Leatherman |
| 5,974,146 A | * | 10/1999 | Randle et al. ................... 705/77 |
| 6,047,268 A | * | 4/2000 | Bartoli et al. ................... 705/35 |
| 6,112,183 A | | 8/2000 | Swanson et al. |
| 6,341,265 B1 | * | 1/2002 | Provost et al. .................... 705/4 |
| 6,484,178 B1 | * | 11/2002 | Bence et al. ........................ 1/1 |
| 7,035,872 B2 | * | 4/2006 | Phillips et al. ...................... 1/1 |

(Continued)

OTHER PUBLICATIONS

Babcock, C., "New Claim Game", Information Week, Feb. 9, 2004, http://www.informationweek.com/story/show/Article.jhtml?articleID=17602359, 3 pages.
Babcock, C., "The Check is . . . Where?", Information Week, Feb. 2, 2004, http://www.informationweek.com/story/show/Article.jhtml?articleID=17601483, 1 page.
Babcock, C., "Doctors Dependent on WebMD Despite Alleged Problems", Information Week, Jan. 29, 2004, http://www.informationweek.com/story/show/Article.jhtml?articleID=17502021, 2 pages.
HIPAA Communicator, WebMD Practice Services, Sep. 2003, vol. 1, 4 pages.
HIPAA Communicator, WebMD Practice Services, Oct. 2003, vol. 2, 4 pages.
Department of Health and Human Services, Federal Register, vol. 65, No. 160, Aug. 17, 2000, Part III.

*Primary Examiner* — Robert R Niquette
(74) *Attorney, Agent, or Firm* — Mannava & Kang, P.C.

(57) ABSTRACT

A direct connectivity system provides automated healthcare administrative transaction submission, including claim submission, eligibility verification and claim status, from healthcare service providers directly to payers. The direct connectivity system bypasses transaction processing intermediaries such as clearinghouses by directly connecting providers to payers in a many to many manner. Existing single payer web portals are supplanted by a many to many network that has a common interface across multiple payers. The direct connectivity system may receive responses directly from payers and may prepare or process the responses for a practice management program so that the service provider receives rapid feedback on the administrative transaction submission. The direct connectivity system may automatically analyze transaction file attributes to determine one or more of many payers to which to send a transaction file, from one of many providers. Batch and singleton file transfer is supported for multiple file formats, optionally with secure file transfer.

15 Claims, 7 Drawing Sheets

(56) References Cited

U.S. PATENT DOCUMENTS

| | | | |
|---|---|---|---|
| 7,356,460 B1* | 4/2008 | Kennedy et al. | 704/9 |
| 2002/0004770 A1* | 1/2002 | Phillips et al. | 705/34 |
| 2002/0120473 A1* | 8/2002 | Wiggins | 705/4 |
| 2002/0147685 A1* | 10/2002 | Kwan | 705/44 |
| 2003/0101111 A1* | 5/2003 | Dang et al. | 705/31 |
| 2004/0078247 A1 | 4/2004 | Rowe, III et al. | |
| 2004/0210521 A1* | 10/2004 | Crea et al. | 705/40 |
| 2004/0215560 A1* | 10/2004 | Amalraj et al. | 705/40 |
| 2004/0236688 A1* | 11/2004 | Bozeman | 705/42 |
| 2006/0041487 A1* | 2/2006 | Santalo et al. | 705/30 |

* cited by examiner

DIRECT CONNECTIVITY SYSTEM FOR HEALTHCARE ADMINISTRATIVE TRANSACTIONS

PRIORITY CLAIM

This application claims the benefit of U.S. Provisional Application Ser. No. 60/583,453, filed Jun. 28, 2004, and titled "Direct Connectivity System for Healthcare Administrative Transactions."

BACKGROUND

1. Technical Field

The present invention relates to communication between data processing systems. In particular, the present invention relates to direct communication of healthcare administrative information and related data between service provider computer systems and payer computer systems.

2. Background Information

Accurate, rapid, and reliable payment of invoices is crucial to every business. When a business generates a consistently large volume of invoices claims, or other transactions, a significant amount of income may become snarled in complex automated claim submission and payment mechanisms. For example, a hospital or other health care provider may have at any given time many hundreds or thousands of claims pending for payments totaling hundreds of thousands or millions of dollars.

Healthcare service providers spend a large quantity of time and effort communicating administrative transactions with health insurance companies. These transactions can include claim submission, member eligibility verification, claim status checks, coordination of benefits with third party payers, remittance advice for final disposition of claims, and notification of payments.

In the past, many providers found that their administrative transactions were unduly delayed because third party clearinghouses handled the transactions. For claim submissions, for example, the clearinghouses acted as middlemen through which claims flowed, with additional processing, to connect payers and providers. Although clearinghouses attempted to address the need for accurate, rapid, and reliable submission of claims, the clearinghouses were often implemented with dated technology that could not meet or perform at acceptable service levels. In addition, the clearinghouses were costly to both the provider and the payer, not only because the clearinghouses took a commission on every claim processed, but also because the clearinghouses sometimes took days to electronically submit claims, failed to communicate claim rejections to the provider, and submitted duplicate and "dirty" claims.

Due in part to the disadvantages of clearinghouses, some business turned to administrative transaction portals, including claim portals. A transaction portal provides a submission interface for the provider into the payer. However, transaction portals were not linked into the providers practice management systems and therefore required time consuming, costly, and error-prone duplicate data entry into the portal. In addition, any response from the payer through the portal required additional processing to be recognized by the payers practice management system. Furthermore, each transaction portal was payer specific and therefore created significant process and change effort for providers.

A need has long existed for addressing the problems noted above and others previously experienced.

BRIEF SUMMARY

Methods and systems consistent with the present invention provide automated administrative transaction submission from service providers directly to payers. The methods and systems determine the appropriate payer for a given transaction file from among many possible payers and bypass transaction processing intermediaries such as clearinghouses and portals. The methods and systems also receive responses directly from the payers and may prepare or process the responses for a practice management program in place at the service provider. The service provider thereby receives rapid feedback to the administrative transaction submission.

In one implementation, a direct connectivity system enhances existing service provider data processing systems. The data processing system may include a communication interface, a memory, and a processor. The memory stores administrative transaction files, transaction file configuration data, and payer connection data. The memory may also include a transaction file submission program executed by the processor.

The transaction file configuration data may associate transaction file attributes, such as filenames or file directories, with payers. The payer connection data may specify payer communication addresses for the payers. In operation, the transaction submission program may include analysis instructions that determine a payer based on the transaction file attributes, as well as transaction transmission instructions that automatically imitate transfer of the transaction file to the determined payer.

In another implementation, a separate direct connectivity gateway interacts with a local service provider data processing system. The gateway may include a communication interface for connecting to the service provider data processing system, a memory, and a processor. The memory may include payer connection data, a file interface program, and a transaction file submission program executed by the processor.

The file interface program may include file transfer instructions that locally transfer transaction files from the service provider data processing system to the gateway. The transaction submission program may then determine a payer from among many payers to which to send the transaction file. In doing so, transaction claim submission program may determine the payer based on an analysis of transaction file attributes and initiate a direct transfer of the transaction file from the provider to the payer.

DETAILED DESCRIPTION

The elements illustrated in the Figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as stored in program, data, or multipurpose system memories, all or part of systems and methods consistent with the direct connectivity solutions may be stored on or read from other machine-readable media, for example, secondary storage devices such as hard disks, floppy disks, and CD-ROMs; electromagnetic signals; or other forms of machine readable media either currently known or later developed.

Furthermore, although this specification describes specific components of a direct connectivity system, methods, systems, and articles of manufacture consistent with the direct connectivity system may include additional or different components. For example, a processor may be implemented as a microprocessor, microcontroller, application specific integrated circuit (ASIC), discrete logic, or a combination of other types of circuits acting as explained above. Databases, tables, configurations, and other data or data structures may be separately stored and managed, incorporated into a single memory or database, or generally logically and physically organized in many different ways. The programs discussed below may be parts of a single program, may be separate programs, or may be distributed across several memories and processors.

Figure 1:
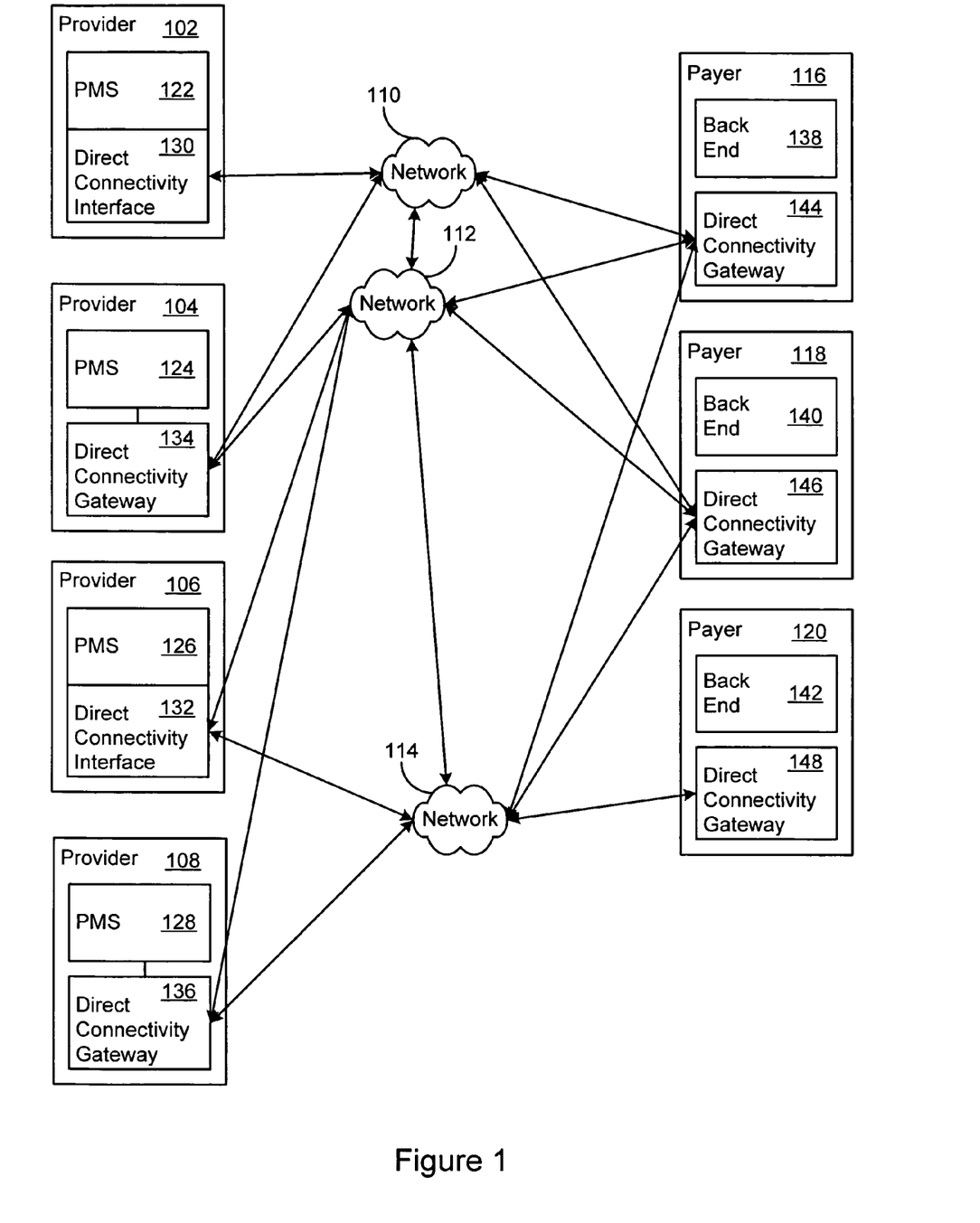
FIG. 1 illustrates service providers directly connected with payers.

FIG. 1 shows service provider data processing systems 102, 104, 106, and 108 ("providers") directly connected through the networks 110, 112, and 114 with payer data processing systems 116, 118, and 120 ("payers"). As will be explained in more detail below, the providers 102-108 employ practice management software 122, 124, 126, and 128 to generate transaction files, including claim files for services rendered to clients. The transaction files may adhere to the National Standard Format (NSF), ANSI X12 file format, or any other claim file format.

The administrative transaction files may contain data for any administrative transaction conducted by a health care provider. As one example, the transaction files may be claim files and functional responses. As other examples, the transaction files may be claim status request and claim status response files, or may be membership eligibility verification request and response files. Additional examples include coordination of benefits files, electronic remittance advice files (e.g. that contains a notification of a final disposition of a claim), and electronic funds transfer notifications. For explanatory purposes, the discussion below uses the specific example of a claim file. However, any other administrative transaction file may instead be processed in the same manner.

The practice management software (PMS) 122-128 may be a physician's office management and medical information system (POMIS). For example, the POMIS may be implemented with the Amicore Practice Management (TM) software available from Amicore, Inc. of Andover, Mass. A provider 102-108 may use any other practice management software available from other vendors, however. The PMS 122-128 may be hosted locally or remotely with respect to the providers 102-108.

In addition to the PMS 122-128, each provider 102-108 includes a direct connectivity solution. As one example, the direct connectivity solution may be a direct connectivity interface 130, 132 to the PMS 122-128. As another example, the direct connectivity solution may be a direct connectivity gateway 134, 136. The interface solution 130-132 and gateway solution 134-136 are described in more detail below.

The direct connectivity solutions 130-136 communicate with the payers 116-120 over one or more of the networks 110-114. The networks 110-114 may adhere to different network topologies and technologies and may be private or public (e.g., part of the Internet). For example, the networks 110-114 may be Ethernet networks, but in other implementations may be implemented with a Fiber Distributed Data Interconnect (FDDI) network, Copper Distributed Data Interface (CDDI) network, or another network technology.

The networks 110-114 may be non-packet switched networks, packet switched networks employing addressed packet communication, or other types of networks in place between the providers 102-108 and the payers 116-120. In other words, the networks 110-114 represent a transport mechanism or interconnection of multiple transport mechanisms for bi-directional data exchange between the providers 102-108 and the payers 116-120.

The payers 116-118 generally include back end processing systems 138, 140, and 142. The back end processing systems 138-142 may represent claim administration or status systems, or other data and systems that the payers 116-118 employ to process submitted claims, track claims, generate status reports, or take other actions. In addition, the payers 116-118 include direct connectivity payer gateways 144, 146, and 148, explained in more detail below.

FIG. 1 shows an example that includes four providers 102-108, three payers 116-120, and three networks 110-1114. However, direct connectivity between providers and payers is not limited to such a configuration. Rather, direct connectivity may connect one or more providers with one or more payers through one or more networks, while bypassing administrative file processing intermediaries such as clearinghouses and portals.

Figure 2:
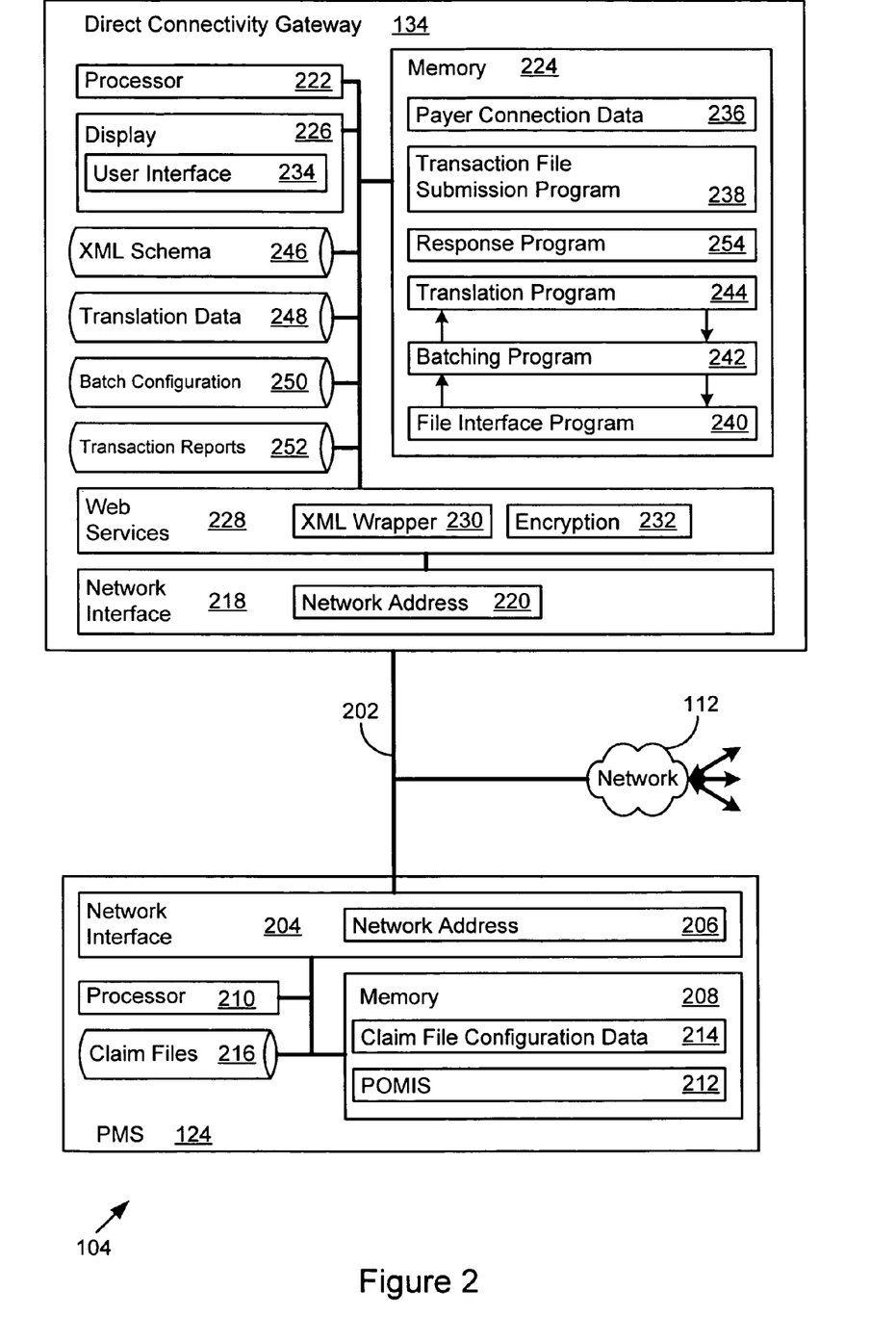
FIG. 2 illustrates one example of a direct connectivity gateway in communication with a service provider data processing system.

Turning next to FIG. 2, that figure illustrates one example of a direct connectivity gateway 134 in communication with a service provider PMS 124 over a local network connection 202. The service provider PMS 124 may include a network interface 204 with an associated network address 206, a memory 208, and a processor 210. The memory holds practice management software such as the POMIS 212 and transaction file configuration data, such as the claim file configuration data 214. According to the configuration entries in the configuration data 214, the POMIS 212 generates claim files 216 with specific file names, in specific directories, in specific file formats, or according to other specified attributes. As noted above, however, the direct connectivity gateway 134 may interoperate with other types of administrative transaction files and may include additional or alternate configuration data that specifies desired attributes of those transaction files.

The gateway 134 may include a network interface 218 with an associated network address 220. The gateway 134 may also include a processor 222, memory 224, and a display 226. A web services layer 228 may also be present and may include an XML wrapper 230 and encryption program 232. The display 226 presents a user interface 234 through which the gateway 134 may communicate or accept transaction status information, such as claims status information, claims processing information, gateway configuration information, or other gateway data through one or more windows, screens, graphical reporting elements, and user input/output elements.

The memory 224 may hold payer connection data 236 and a transaction file submission program 238. The memory 224 may also hold a file interface program 240, a batching program 242, and a translation program 244. In operation, the gateway 134 may access an XML schema 246, translation data 248, batch configuration data 250, and transaction reports 252.

The service provider PMS 124 may represent a data processing installation on-site at the service provider. The gateway 134 may be a separate data processing system installed locally at the service provider and connected to the PMS 124 through the local network connection 202. The network interfaces 204, 218 may also provide access to the external network 112.

The PMS 124 and the gateway 134 communicate through their network interfaces 204, 218. To that end, the network addresses 206, 220 may be a packet switched network destination identifier, or a destination address for any other type of network or network protocol. For example, the network addresses 206, 220 may be a Transmission Control Protocol/Internet Protocol (TCP/IP) address (optionally including port numbers).

The processor 210 in the PMS 124 executes the practice management software 212. According to the claim file configuration data 214 and the inputs from the service provider, the POMIS software 212 generates the claim files 216. The claim file configuration data 214 may represent internal software settings configured in the POMIS software 212, may be a separate configuration file stored in the memory 208, or may take another form.

Figure 3:
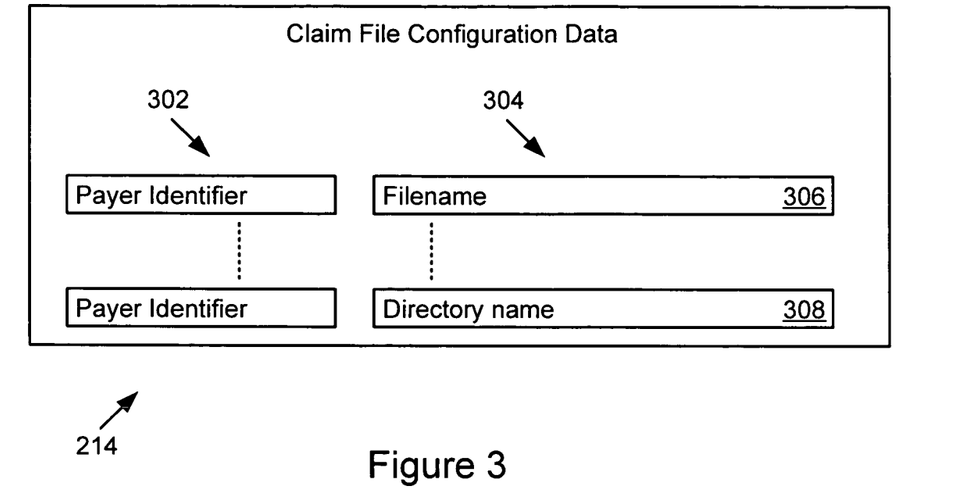
FIG. 3 shows one example of claim file configuration data.

Turning briefly to FIG. 3, that figure shows one example of the configuration entries that may be present in the claim file configuration data 214. For example, the claim file configuration data 214 may include payer identifiers 302 associated with claim file attribute entries 304. The claim file attribute entries 304 may specify attributes of a claim file prepared for any given payer. For example, the attribute entries 304 may include a filename entry 306, a directory name entry 308, or other file attribute entries discussed below.

The POMIS software 212 may generate claim files for many payers. Accordingly, the claim file configuration data 214 may direct the POMIS software 212 to generate a claim file with attributes specified by the attribute entries 304. For example, a payer identifier may be a string or numeric identifier that represents ACME insurance, and the associated attribute data may be a filename such as "ACME_insurance_claim_file.txt." In response, the POMIS software 212 saves the claim data for ACME insurance claims in a file named "ACME_insurance_claim_file.txt." Alternatively, the administrative transaction information for multiple payers may be stored in a single file, with an identifier with each record that determines to which payer the administrative transaction should be sent.

Returning to FIG. 2, the gateway 134 executes the file interface program 240 to retrieve claim files 216 from the PMS 124. The interface program 240 may include a File Transfer Program (FTP) or any other type of file transfer mechanism. The file interface program 240 may automatically execute according to a periodic or non-periodic schedule to check for new claim files saved on the PMS 124. In one implementation, the interface program 240 may poll specified directories for one or more file types saved under or more naming conventions. The interface program 240 may access networked drives, for example, through the HTTP protocol.

The batching program 242 optionally batches together transaction files for efficient transfer to payers. The batching program 242 may read the batch configuration data 250 to obtain a maximum or minimum file size for a batch, a maximum or minimum number of individual files to batch together, a time delay for how long to wait before sending a batch of files, or any other batching parameter. The batching program 242 may concatenate transaction files, add them to a common carrier such as an archive file, or may batch transaction files together using other techniques.

The translation program 244 may optionally translate a transaction file or batch of transaction files from one format to any other format. The translation program 244 may read the translation data 248 to determine translation rules for converting between file formats. For example, the translation program 244 may translate X12 format claim files to NSF format claim files. In general, the translation program 244 may keep selected data entries, delete selected data entries, specify data entries to be included in the translated file, change the representation of data entries (e.g., from numeric to string), or may apply any other translation operations.

When the gateway 134 obtains the claim files, the gateway 134 executes the transaction file submission program 238 to send the claim files to the appropriate payers. In that regard, the transaction file submission program 238 acts as a switch to transfer claim files directly to one or more of multiple payers. The transaction file submission program may 238 may include claim file attribute analysis instructions that consult a local copy of the claim file configuration data 214 to match a claim file characteristic (or a characteristic of any other transaction file) to a payer. In other words, the transaction file submission program 238 may analyze and determine from filenames, directory names, or other file characteristics, a payer identifier representing a payer to which the claim file should be sent. In addition, the transaction file submission program 238 may consult the payer connection data 236 to determine a payer address to which to send a claim file.

In other implementations, the transaction file submission program 238 may consult additional or alternative information than file characteristics to determine to which payer to send an administrative transaction file. In that regard, the transaction file submission program 238 may examine entries in the transaction file itself, entries in individual transaction files batched together in a batch file, separate administrative messages or data, or other payer identification data. As one example, the transaction file, a Payer ID entry may specify to which payer a transaction file should be transmitted.

Figure 4:
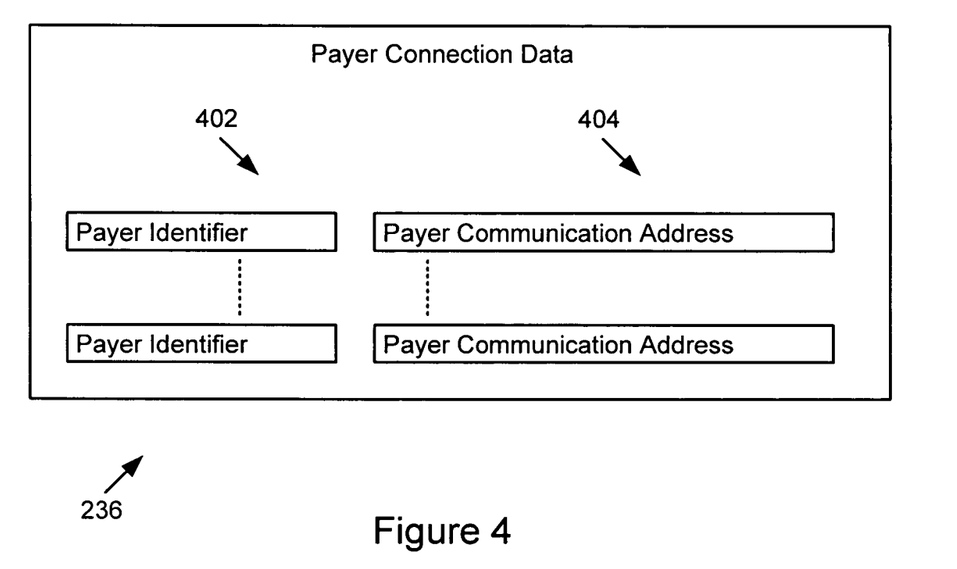
FIG. 4 shows an example of payer connection data.

Turning briefly to FIG. 4, that figure shows one example of the payer connection entries that may be present in the payer connection data 236. For example, the payer connection data 236 may include payer identifiers 402 associated with payer communication address entries 404. The payer communication address entries 404 may specify network addresses, port numbers, or other destination attributes for a payer. For example, a payer identifier for ACME insurance may be associated with an IP address and port number.

With regard again to FIG. 2, the transaction file submission program 238 may execute claim transmission instructions to initiate transfer of the claim files directly to the payers. In other words, the transaction file submission program 238 bypasses conventional claim processing intermediaries such as clearinghouses and portals. Instead, the transaction file submission program 238 transmits the claim files through the network 112 to the payers for direct reception and processing as will be explained in more detail below.

Optionally, the web services layer 228 may execute the XML wrapper 230 to apply extensible markup language (XML) tags to all or part of the transaction file data or other data transmitted from the gateway 134. The XML wrapper 230 may also remove XML tags from data received by the gateway 134 such as response data from payers. The XML wrapper 230 may apply or remove XML tags specified by the XML schema 246. In one implementation, the XML schema 246 specifies a set of rules for semantic tags that describe the claim file data, including start tags, end tags, attributes, and other XML elements tailored for health care claims, or any other type of claims or transaction file.

In addition, the web services layer 228 may execute the encryption module 232 to encrypt or decrypt any data transmitted through the network interface 218. For example, the encryption module 232 may apply a public key infrastructure encryption or decryption to a claim file, to batches of claim files, to XML tagged claim files, or other data. The web services layer may also execute a program to manage the messaging over the network in a reliable manner, by persisting requests in memory until an acknowledgement has been received, and sending acknowledgements to the proper payer when a response has been received.

The transaction reports 252 may store reporting records for the gateway 134. For example, the transaction reports 252 may store data transmission error records. As other examples, the transaction reports 252 may store data transfer statistics such as time, date, byte count, encryption, or other statistics, may store claim file names of files retrieved from the CMS 124, batching statistics, or any other reporting or statistic data for the gateway 134.

Many different technologies may be employed to implement the gateway 134. For example, the gateway may be a Microsoft Windows (TM) machine executing the .NET (TM) framework, employing MSXML Core Services for local data stores, or employing SQL server technology. The web services 228 may be provided by a Windows 2003 server under the .NET framework and Internet Information Server (IIS), with support programs for encryption and MSXML tools for XML application or parsing. The Organization for the Advancement of Structured Information Standards (OASIS) WS-Security or WS-Reliable Messaging protocols may be employed for secure data storage and access or data transmission between payers and providers. Objects may be stored or access according to the Simple Object Access Protocol (SOAP). SOAP standards may be found online at www.w3.org/TR/soap.

In many instances, the gateway 134 may receive administrative transaction responses through the network interface 218. For example, a payer may reply in real time or non-real time to the direct submission of claim files with acknowledgements, status updates, claim file format error messages, processing messages, claim status indicators, or other response data. In one implementation, the claim response program 254 accepts and processes the responses from payers.

To that end, the response program 254 may include reception instructions that receive the response from the payer. The response program 254 may also include push instructions that configure the response for the practice management program, such as the POMIS software 212, in the system 124. The push instructions may then transmit the optionally reconfigured response to the system 124 for automated processing by the POMIS software 212.

The push instructions may configure the response by modifying any characteristic of the response or its attributes. As an example, the push instructions may store the response according to a filename, directory name, or any other file attribute expected for response by the POMIS software 212. As another example, the push instructions may include instructions that format, in the same or similar manner as the translation program 244, the response data according to an expected format for the POMIS software 212.

Figure 5:
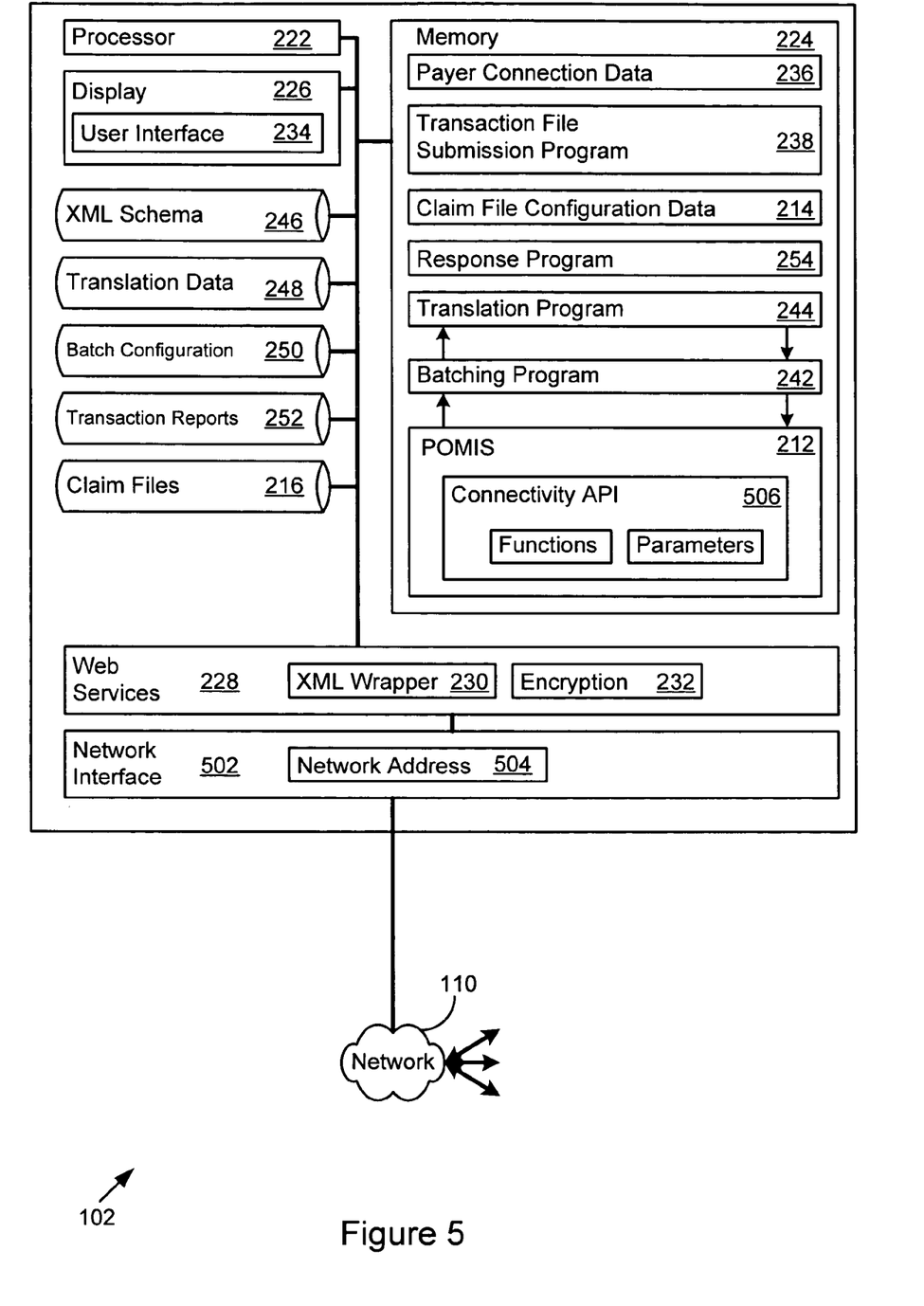
FIG. 5 illustrates one example of a direct connectivity interface operating in conjunction with a practice management program in a service provider data processing system.

Turning next to FIG. 5, that figure shows another example of a direct connectivity solution. In particular, FIG. 5 shows a more detailed view of the provider 102 with the direct connectivity interface 130. Like the direct connectivity solution presented in FIG. 2, the provider 102 directly sends administrative transaction files to payers through the network interface 502 associated with the network address 504.

In FIG. 5, however, the direct connectivity solution is integrated in the data processing system that executes the POMIS software 212. Accordingly, rather than connecting a separate gateway 134 to a PMS data processing system 124 through a local network connection 202, the provider 102 may instead integrate the direct connectivity processing into or with the POMIS software 212 in a data processing system. As a result, the direct connectivity solution has local access to claim files and need not initiate their transfer to a separate gateway.

In one implementation, the POMIS software 212 is compiled with or otherwise includes or has access to a connectivity application programming interface (API) 504. The API 504 may provide the calling convention by which the POMIS software 212 may access direct connectivity services through a formalized set of software calls and routines. Accordingly, the API 504 may define one or more function calls and parameter lists to direct connectivity functions.

As one example, the API 504 may define a function call that the POMIS software 212 may make to initiate submission of claim files by the transaction file submission program 238. As another example, the API 504 may define a function call that the POMIS software 212 may make to initiate execution of the response program 254. In other implementations, however, the POMIS software 212 may instead or additionally directly initiate execution of the direct connectivity programs.

The operation of the elements present in FIG. 5 may follow the description above with reference to FIGS. 2-4. As an example, the provider 102 may optionally batch transaction files for transmission to a payer. In addition, the provider 102 may apply or remove XML tags from data transmitted or sent through the network interface 218, and may apply or remove encryption. The provider 102 may also maintain the transaction reports 252 and translate claim data according to the translation data 248.

Figure 6:
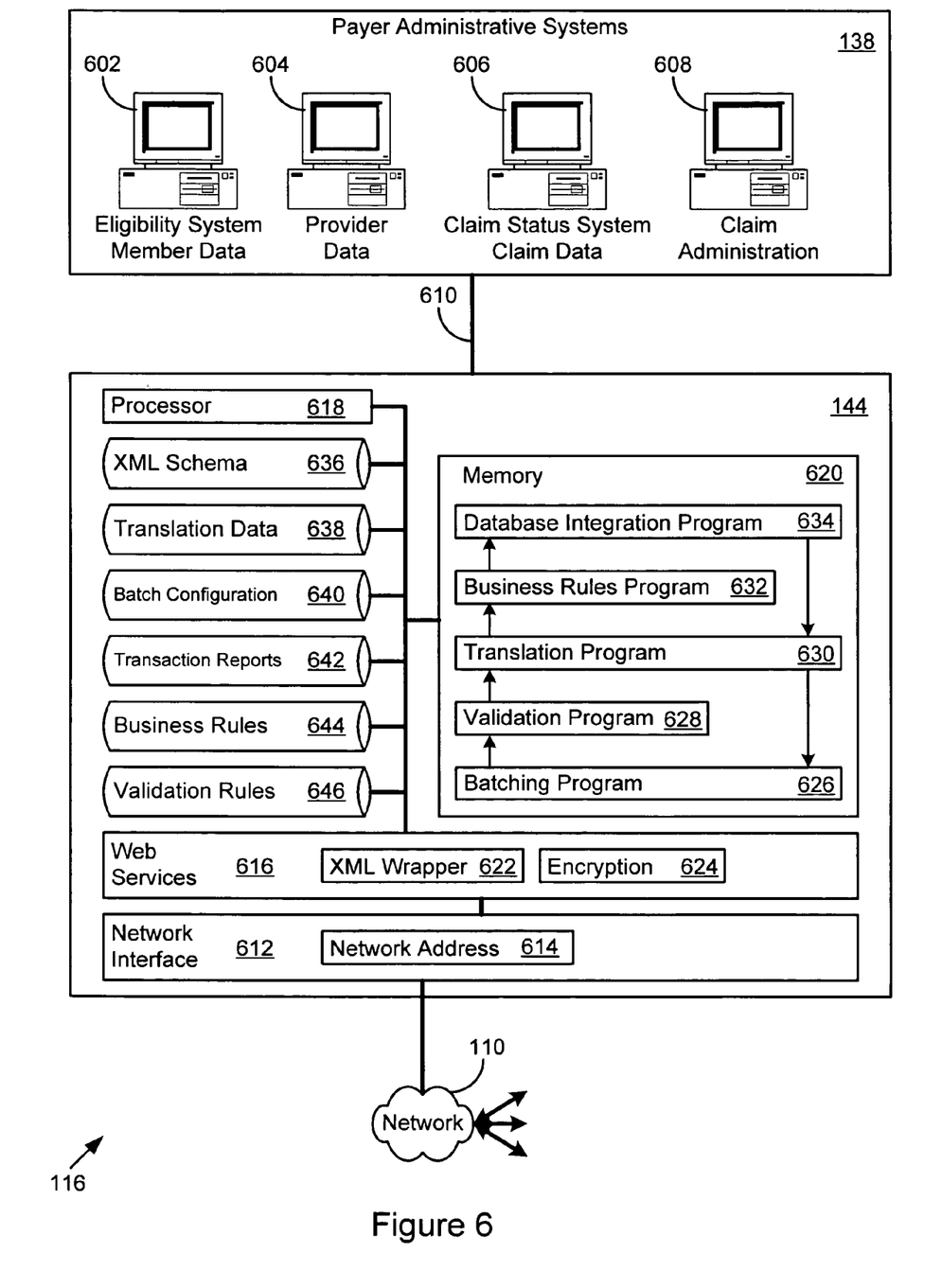
FIG. 6 shows one example of a payer data processing system that includes a back end system and a direct connectivity gateway.

With regard next to FIG. 6, a more detailed view of example implementation of the payer 116 is presented. The payer 116 may include one or more back end systems 138, such as payer administrative systems. The back end systems 138 may include, as examples, a member eligibility system 602, a provider data system 604, a claim status system 606 and a claim administration system 608. The payer 116 employs the back end systems 138 to validate, process, and pay claims received from providers, as well as to generate status reports for claim payments, determine eligibility for providers or their clients, generate error reports for rejected claims, and to perform other related tasks.

The payer 116 also includes a direct connectivity gateway 144 connected to the back end systems 144, for example, through a local network connection 610. The direct connectivity gateway 144 includes a network interface 612 with one or more network addresses 614. The network interface 612 may support the local network connection 610 and also provide a connection to the network 110. The gateway 144 also includes a web services layer 616, a processor 618, and a memory 620. The web services layer 616 may include an XML wrapper 622 and encryption program 624.

The memory 620 may include a batching program 626, a validation program 628, and a translation program 630. In addition, the memory may include a business rules program 632 and a database integration program 634. The payer gateway 144 may also maintain or include an XML schema 636, translation data 638, and batch configuration data 640. In addition, the payer gateway 144 may include transaction reports 642, business rules 644, and validation rules 646.

The discussion below addresses the specific example of a payer 116 processing a claim file. However, the payer 116 may process any other administrative transaction file instead, including those noted above in the discussion of the direct connectivity aspects of the provider systems.

In the same manner explained above on the provider side, the payer side web services layer 616 may employ the XML wrapper 622 to apply or remove XML tags to all or part of the transaction file data received, or to all or part of response data sent back to the providers. The XML wrapper 622 may apply or remove XML tags specified by the XML schema 636. In one implementation, the XML schema 636 specifies a set of rules for semantic tags that describe the response data or claim file data, including start tags, end tags, attributes, and other XML elements. In addition, the web services layer 616, through the encryption module 624, may encrypt or decrypt any data transmitted through the network interface 612, including responses sent back to the providers 102-108. The web services layer may also execute a program to manage the messaging over the network in a reliable manner, for example by persisting responses in memory until an acknowledgement has been received, and sending acknowledgements to the proper provider when a response has been received.

The payer gateway 144 directly receives claim files transmitted from the providers 102-108. To that end, the payer gateway 144 may execute the batching program 626 to coordinate reception of batches of claim files. The batching program 626 may read configuration information from the batch configuration data 640 that may, as examples, specify batch file size parameters, file formats, or other batch configuration information to assist the batching program 626 with extracting individual claim files from a batch of claim files.

The gateway 144 may also provide validation services on the received claim files. For example, the gateway 144 may execute the validation program 628. The validation program 628 may read the validation rules 646 and apply the validation rules 646 to the received claim files. As examples, the validation rules may dictate that data fields include a data value of the appropriate type (e.g., a numeric field must include a numeric data value), that required data fields (e.g., name, address, or contact information fields) actually contain data, or that other information is present, or that claim files adhere to specified protocols, formats, or other standards, such as the X12 or NSF file standards.

In a manner similar to that explained above, the payer gateway 144 may also execute the translation program 630 to convert received claim files to a format expected by any back end processing system 602-608. In that regard, the translation program 630 may access translation data or translation rules 638. The translation rules 638 may specify the steps to be taken or conversions to be executed by the translation program 630 to convert one file format to another file format. For example, the translation rules 638 may specify that data fields are to be converted from numeric to string fields, that numeric fields or string fields are to be truncated or expanded, or may specify other file format conversion rules.

The payer gateway 144 may perform additional checks on the claim files. In one implementation, the payer gateway 144 executes the business rules program 632 to examine specific characteristics of the claim files. The business rules 644 may specify expected data characteristics for the claim files. As one example, the business rules 644 may require that a claim dollar amount be between specified limits. As another example, the business rules 644 may require that diagnostic codes in the claim file are standards-approved diagnostic codes. In other words, the business rules program 632 may substantively examine the claim data content to determine whether the claim data may be processed by the payer 116.

The database integration program 634 provides an interaction layer that communicates with the back end 138. The integration program 634 may submit or store a claim into the claim status system 606, for example. The integration program 634 may prepare database read or write requests according to the format expected by one or more of the back end systems 138. As examples, the integration program 634 may frame data transfer requests to the back end 138 or receive data from the back end 138 according to File Transfer Protocol, Hypertext Transfer Protocol, an Oracle database format, DB2 database format, IBM WebSphere MQ messaging protocol, Vertical Storage Access Method (VSAM) database format, Customer Information Control System (CICS) transaction protocol, or any other data format, messaging protocol, or transaction control protocol.

Transaction files such as claim files received at the payer gateway 144 may give rise to a response from the payer gateway 144 to the provider indicating that the claim was received at the payer. Similarly, transaction files submitted to the back end 138 for processing may give rise to a response to the provider indicating that the transaction file is being processed at the payer. For example, when a claim is rejected, during the validation or business rules processing, the payer may generate a response to the provider indicating that the claim has been rejected. The payer 116 may prepare and send other responses for claim files or for other types of transactions to the providers as well.

Regardless of the source or nature of a response, the payer 116 may optionally tag the response (e.g., with XML tags), encrypt the response, and send the response directly back to the provider. The provider may then receive the response, remove the tags, decrypt the response, and store the response for additional processing by claims management software or by another application. Accordingly, the providers 102-108 and payers 116-120 may engage in direct bi-directional communication regarding transaction files.

The transaction reports 642 may store reporting records for the payer gateway 144. As noted above, transaction reports may store data transmission error records, data transfer statistics such as time, date, byte count, encryption, reasons for claim rejections, validation errors, business rule errors, internal errors, claim file names, file lengths, provider identifiers, batching statistics, claim counts, or any other reporting or statistic data.

The payer gateway 144 may be implemented in part with Microsoft operating systems such as Windows XP (TM), Windows 2003 server operating under the .NET framework, and may include an Internet Information Server (IIS). Additionally or alternatively, the payer gateway 144 may implement one or more of the programs 626-634 with commercial software packages such as BizTalk server, BizTalk adapter for web services, or BizTalk accelerator for HIPAA available from Microsoft. As another example, Microsoft MSXML Parser or Core Services may provide support for the XML wrapper 622, XML tags, and XML schemas.

Figure 7:
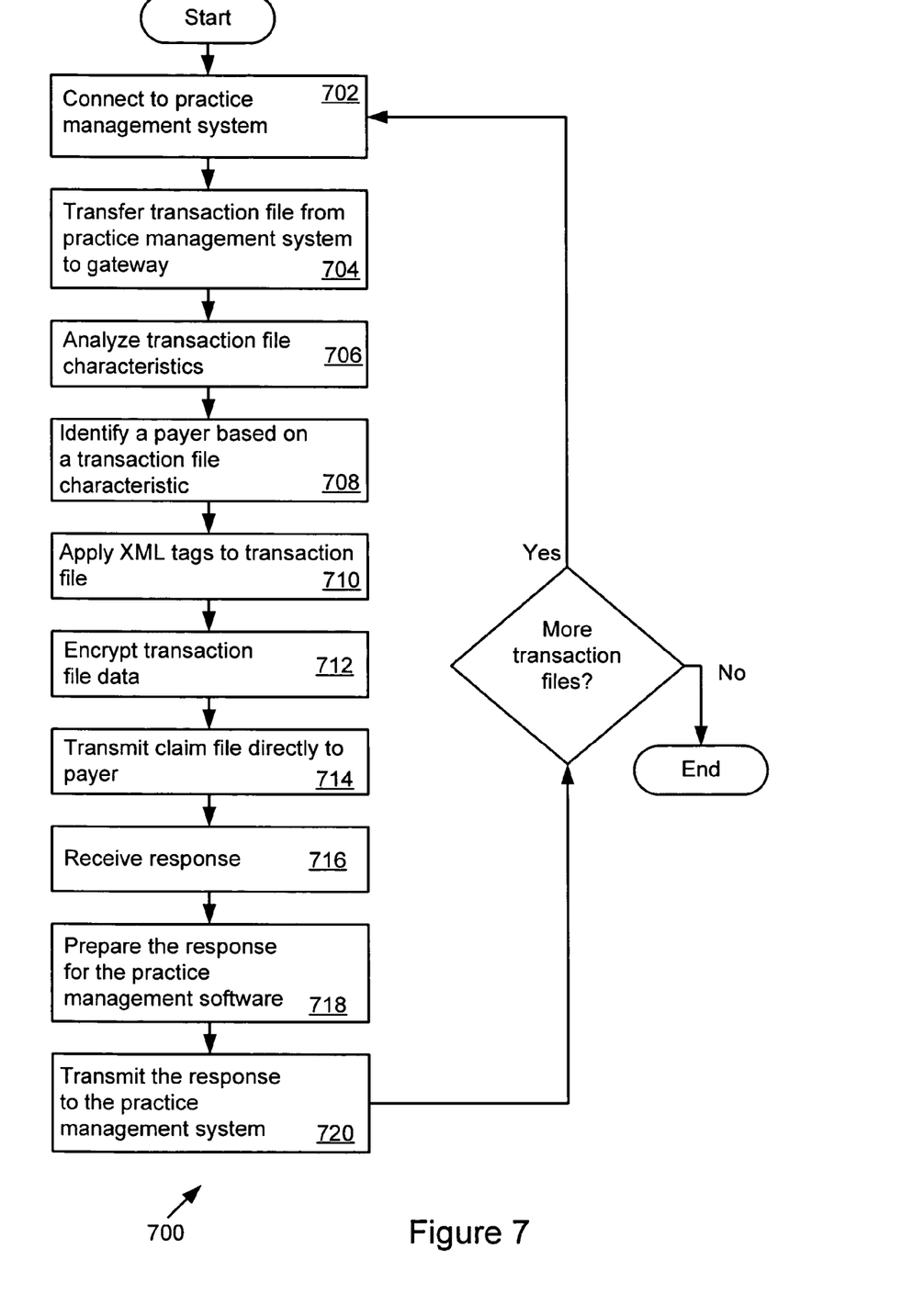
FIG. 7 shows one example of the acts that a direct connectivity gateway may take to transfer files directly between a service provider and a payer.

FIG. 7 shows one example of the acts 700 that a direct connectivity gateway (e.g., the gateway 134) may take to transfer administrative transaction files directly between a service provider 104 and a payer 116. The gateway 134 connects to a service provider practice management data processing system 124 (Act 702). A file transfer interface 240 in the gateway 134 then transfers one or more transaction files from the system 124 into the gateway 134 (Act 704).

A transaction file submission program 238 in the gateway 134 may then analyze transaction file characteristics (Act 706). Based on the transaction file characteristics the transaction file submission program 238 may identify a payer in payer connection data 236 to which the transaction file should be transmitted (Act 708). As examples, the transaction file submission program 238 may index or lookup a filename, directory name, or other attribute in the payer connection data 236 and determine an associated payer communication address.

The gateway 134 may also apply markup tags to all or part of a transaction file (Act 710). For example, the tags may be XML tags. In addition, the gateway 134 may optionally encrypt transaction file data prior to transmission to the payer (Act 712).

The gateway 134 transmits the transaction file directly to the payer 116 (Act 714). The claim file may propagate along one or more external networks, but bypasses processing by intermediary claim processing entities such as clearinghouses. The transaction file arrives at and is processed by the payer 116.

The gateway 134 may also receive a response from the payer 116 (Act 716). The gateway 134 may responsively prepare the response, for example, by modifying any of its characteristics, data, or attributes to format the response for the practice management program running in the provider 104 (Act 718). The gateway 134 may then communicate the response back to the service provider practice management data processing system 124 (Act 720).

Figure 8:
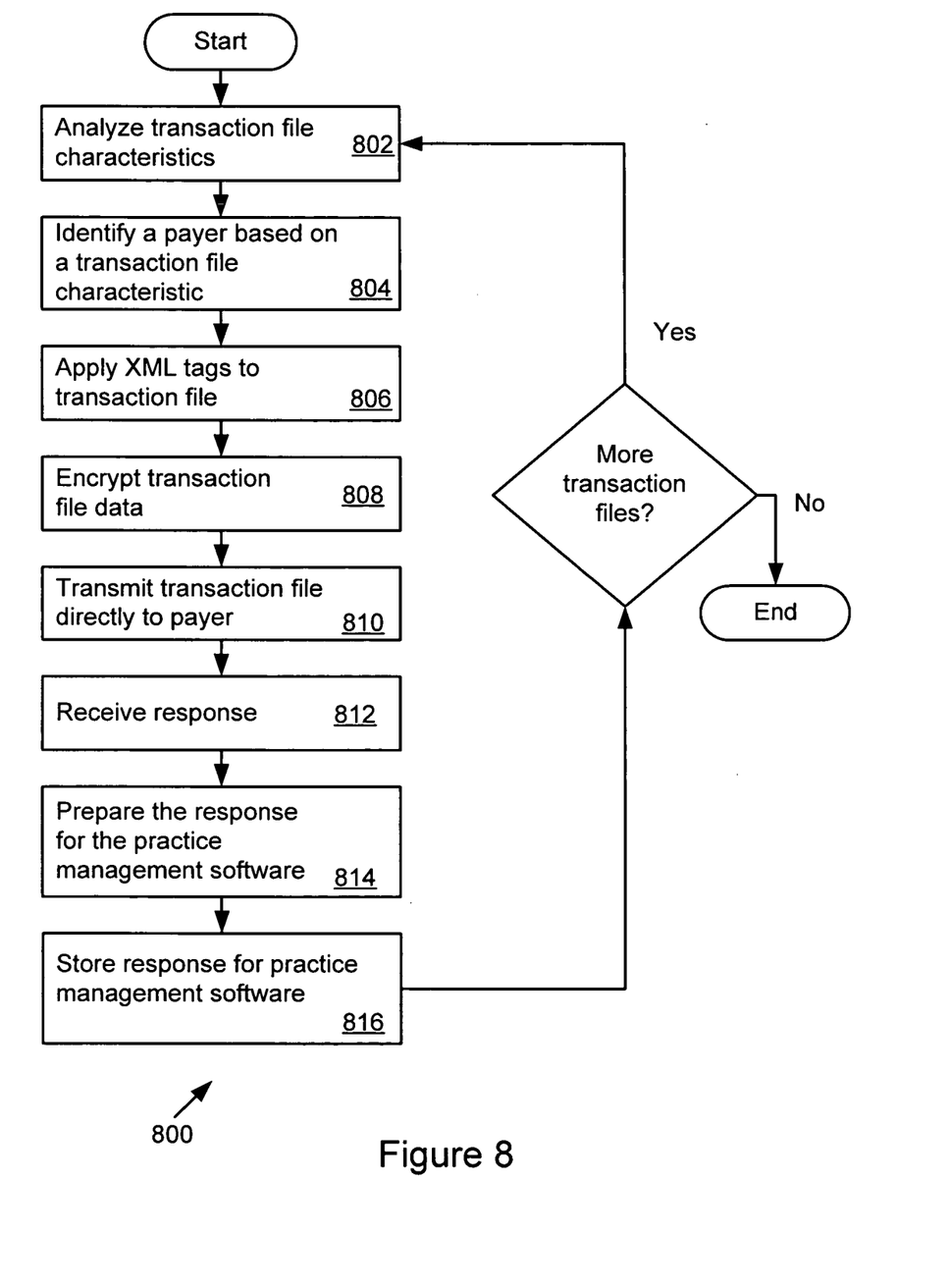
FIG. 8 shows an example of the acts that a direct connectivity interface may take to transfer files directly between a service provider and a payer.

FIG. 8 shows an example of the acts that a direct connectivity interface may take to transfer transaction files directly between a service provider 1012 and a payer 116. Because the direct connectivity interface may be integrated with the service provider practice management data processing system 102, the interface need not transfer transaction files to a gateway.

Instead, the practice management software may execute function calls to direct connectivity functions, procedures, or other programs through an API 506. For example, after the practice management software has prepared a transaction file, the practice management software may initiate execution of direct connectivity functions directly or through the API 506.

Accordingly, in the operation of a direct connectivity interface such as that shown in FIG. 5, a transaction file submission program 238 may analyze transaction file characteristics (Act 802). Based on the transaction file characteristics, the transaction file submission program 238 may index or lookup a payer in payer connection data 236 to which the transaction file should be transmitted (Act 804). However, as noted above, the transaction file submission program 238 may consult other data sources, including a Payer ID field in a transaction file, to determine an appropriate payer. The provider 102 may optionally apply markup tags to all or part of the transaction file (Act 806) and may optionally encrypt transaction file data prior to transmission to the payer (Act 808).

The provider 102 transmits the transaction file directly to the payer 116 (Act 810), bypassing intermediary transaction file processing entities. The provider 102 may also receive a response from the payer 116 (Act 812) and modify the response in a manner appropriate for the practice management software (Act 814). The response is then stored using a particular filename, directory, or other file attribute expected by the practice management software (Act 816).

As noted above, the direct connectivity solutions may apply to data other than claim data. As examples, payers may providers may be directly linked and bi-directionally transfer claim rejections, claim notifications, claim status, eligibility data, electronic fund transfers, instant messages, or other data.

The direct connectivity solutions may interoperate with many different file formats. As examples, the claim files and responses may adhere to the X12 file format including the 837 (4010) format for professional and institutional claim submission, and the 997 format for functional acknowledgment. As another example the claim files and responses may adhere to the NSF file format including the HCFA NSF v3.01 format for claim submission, the UB-92 v6.0 format for professional claim submission, or the HCFA format for flat file functional acknowledgement.

Data transmitted between providers 102-108 and payers 116-120 may occur synchronously, with immediately available functional reply and receipt acknowledgements; asynchronously, with immediately available acknowledgement, delayed functional reply, polling for outstanding responses, and receipt acknowledgements; or in a multi-part manner both asynchronously, with immediately available acknowledgement for a sequence of requests, and with delayed functional replies.

The data transmission may occur under the WS-Reliable Messaging standard. The WS-Reliable Messaging standard offers message sequences for multi-part asynchronous data transfer and a N-Ack for immediate no acknowledgement and a timeout period if no acknowledgement is received. The providers 102-108 and payers 116-120 may implement message persistence to maintain messages until an acknowledgement is received. For example, a provider may persist messages in a local store until an acknowledgement is received, and a payer may persist a response until acknowledgement is received from a client or provider.

A payer 116-120 may implement a Mailbox for each of its trading partners (e.g., each provider that the payer interacts with) to hold outgoing messages. The messages may remain or persist in the Mailbox until the trading partner has confirmed their receipt with a receipt acknowledgement. The messages in the Mailbox may include a sequence and message number to confirm receipt.

Table 1, below, shows header fields that may be employed in data messages sent between providers 102-108 and payers 116-120:

TABLE 1

| Field | Explanation |
| --- | --- |
| Sequence Number | For multi-part requests |
| Message Number | For multi-part requests |
| Correlation Id | May be generated in request and matched in response |
| Format | X12, NSF, XML, or another format identifier |
| Type | 837, 835, or another message type |
| Version | Format and type specific version |
| Source TP Id | "From" field |
| Destination TP Id | "To" field |
| Source TP type | Payer, Provider, Broker, Group, or other type identifier |
| Destination TP type | Payer, Provider, Broker, Group, or other type identifier |

TABLE 1-continued

| Field | Explanation |
|---|---|
| Security/Credentials | PKI, HTTPS, or other security credentials |

The direct connectivity solutions may also provide reports and support queries based, for example, on the transaction reports 252. For example, the reports may include an Activity Summary report that shows the total volume of submissions by date range and type, including total claim volume and total rejected claims; an Activity by Provider report that shows a detail report of activity by provider identifier and date range, optionally including batch header information such as total claims in each submission and number of rejected claims; an Error Summary report that shows a breakdown of errors and rejections organized by error code for a date range and submission type (e.g., for claims submissions, eligibility queries, or other data submissions); and an Errors by Provider report that shows a breakdown of errors and rejects by error code for a provider by date range and submission type.

The user interface 234 may define a transmission status view screen that shows, as examples, a view for all types of transmissions; locally pending submissions and types; submissions pending functional responses; current activity (e.g., currently sending a claim file or receiving a response); and internet or network status (e.g., connected disconnected, available, or any other status).

The user interface 234 may also define a configuration screen with input and output user interface elements. The user interface elements may accept or report general direct connectivity parameters, payer parameters (e.g., payer connection data), file interface parameters, or other configuration information.

The user interface 234 also may include claim error screens. The claim error screens may show all functional acknowledgements that have been saved locally. The functional acknowledgements may include an activatable link to underlying detail, and may also provide a deletion mechanism to delete locally saved functional acknowledgements. An additional claim error screen may provide detail views and navigation of individual functional acknowledgement records.

Provider configuration data may be stored in a standard location, for example, based on the installation directory of nay direct connectivity programs. For example, a persistence location may be specified as {$DirConnInstall$}/persistence, where $DirConnInstall$ represents the installation directory. For each file type or file format supported by the direct connectivity solutions, the provider may store configuration data shown below in Tables 2 and 3.

TABLE 2

| Request file (e.g., claim file) configuration data |
|---|
| Polling Interval |
| Request file location |
| Request file format |
| Request file type |
| Request file version |
| Request file naming convention that may distinguish payers, including payer identifier, date-time stamp, unique sequence number, or other fields. |

TABLE 3

| Response file configuration data |
|---|
| Response file location |
| Response file format |
| Response file type |
| Response file version |
| Response file naming convention that may distinguish payers, including payer identifier, date-time stamp, unique sequence number, or other fields. |
| Save Response locally flag |

The payer connection data 236 may be more generally represented with payer configuration data that may include fields such as those shown below in Table 4.

TABLE 4

| Response file configuration data |
|---|
| Payer Name (e.g., for display) |
| Payer Identifier (Trading Partner Identifier) |
| Trading Partner Type (Payer) |
| Security Configuration data (e.g., PKI configuration) |
| File Formats Supported: |
|     Format |
|     Type |
|     Version |
|     Messaging Protocols supported (e.g., synchronous, asynchronous, multi-part asynchronous) for each format/type |
|     Timeout period for resubmission of data |
| Messaging Information |
|     URI |
|     Ports |

The direct connectivity solutions eliminate intermediary transaction file processors such as clearinghouses by providing automated transaction file submission from service providers directly to payers. The direct connectivity solutions may provide real time or near real time transmission of transaction file data to payers and real time or near real time transmission of responses to providers. Accordingly, providers and payers may experience more accurate, rapid, and reliable submission and payment of claims and other administrative transactions, reduce costs, and the occurrence of duplicate claims or "dirty" claims or other transactions.

It is therefore intended that the foregoing detailed description be regarded as illustrative rather than limiting, and that it be understood that it is the following claims, including all equivalents, that are intended to define the spirit and scope of this invention.

The invention claimed is:

1. A non-transitory machine readable medium encoded with instructions that cause a service provider data processing system to perform a method comprising the acts of:
   determining that an administrative transaction file has been prepared by a practice management program, wherein the administrative transaction file includes a predetermined file attribute specified by administrative transaction file configuration data that includes a plurality of predetermined file attributes associated with payer identification information for multiple payers;
   determining, using the predetermined file attribute of the transaction file, payer identification information for a selected payer associated with the transaction file from the payer identification information for multiple payers;
   determining, using the payer identification information for the selected payer, payer communication data for the selected payer;

initiating transmission of the transaction file from a hardware implemented direct connectivity gateway to the selected payer of the multiple payers using the determined payer communication data, thereby bypassing transaction file processing intermediaries;

receiving, at the hardware implemented direct connectivity gateway, a response from the selected payer to the transmission of the transaction file; and configuring the response for the practice management program by modifying attributes of the response for automated processing by the practice management program.

2. The machine readable medium of claim 1, where the predetermined file attribute is a filename.

3. The machine readable medium of claim 1, where the predetermined file attribute is a file directory.

4. The non-transitory machine readable medium of claim 1, further comprising applying extensible markup language tags to all or part of the transaction file.

5. The non-transitory machine readable medium of claim 1, wherein the modified attributes of the response include a filename or a directory name.

6. The non-transitory machine readable medium of claim 1, wherein the modified attributes of the response include a format of the response.

7. The machine readable medium of claim 1, wherein the response is based on a determination by the selected payer of whether an amount associated with a claim associated with the administrative transaction file is between specified limits.

8. A non-transitory machine readable medium encoded with instructions that cause a hardware implemented direct connectivity gateway to perform a method comprising the acts of:

connecting to a service provider data processing system through a communication interface;

determining that a transaction file has been prepared on the service provider data processing system by a claim management program;

transferring the transaction file to the hardware implemented direct connectivity gateway;

obtaining a selected file attribute of the transaction file;

reading payer connection data to determine a selected payer of multiple payers for the transaction file according to attribute data that associates file attributes, including the selected file attribute, with the multiple payers, including the selected payer, wherein the selected file attribute is a predetermined file attribute specified by administrative transaction file configuration data that includes a plurality of the file attributes associated with payer identification information for the multiple payers;

initiating transmission of the transaction file from the hardware implemented direct connectivity gateway to the selected payer of the multiple payers, thereby bypassing transaction file processing intermediaries;

receiving, at the hardware implemented direct connectivity gateway, a response from the selected payer to the transmission of the transaction file; and configuring the response for the claim management program by modifying attributes of the response for automated processing by the claim management program.

9. The machine readable medium of claim 8, where the act of connecting to the service provider data processing system comprises the act of connecting to a service provider data processing system co-located with the hardware implemented direct connectivity gateway.

10. The machine readable medium of claim 8, where the predetermined file attribute is a filename.

11. The machine readable medium of claim 8, where the predetermined file attribute is a file directory.

12. The machine readable medium of claim 8, wherein reading payer connection data to determine a selected payer for the transaction file according to attribute data that associates transaction file attributes, including the selected file attribute, with multiple payers, including the selected payer comprises:

determining, using the selected file attribute of the transaction file, the payer identification information for the selected payer from the multiple payers; and determining, using the payer identification information for the selected payer, the payer connection data for the selected payer.

13. The machine readable medium of claim 8, wherein initiating transmission of the transaction file to the selected payer of the multiple payers, thereby bypassing transaction file processing intermediaries comprises:

initiating the transmission of the transaction file to the selected payer using the payer connection data.

14. A system operable to provide connectivity to a payer computer system, the system comprising:

a processor; and data storage storing claims configuration information for multiple payers, the claims configuration information including, for each payer, payer identification information, a file attribute, and payer communication data, wherein the processor determines a transaction file has been prepared by a practice management program, wherein the administrative transaction file is created using the claims configuration information, determines a selected file attribute of the transaction file, wherein the selected file attribute is one of the file attributes in the claims configuration information, determines, using the selected file attribute of the transaction file, the payer identification information corresponding to the selected file attribute from the claims configuration information;

determines, using the payer identification information, the payer communication data corresponding to the payer identification information from the claims configuration information, initiates transmission of the transaction file from a hardware implemented direct connectivity interface to a payer identified by the payer identification information using the determined payer communication data, thereby bypassing transaction file processing intermediaries, receives, at the hardware implemented direct connectivity interface, a response from the selected payer to the transmission of the transaction file, and configures the response for the practice management program by modifying attributes of the response for automated processing by the practice management program.

15. The system of claim 14, wherein the selected file attribute comprises at least one of a filename and a file directory.

* * * * *